(12) United States Patent
Zhou et al.

(10) Patent No.: US 11,560,411 B2
(45) Date of Patent: Jan. 24, 2023

(54) USE OF RECOMBINANT HUMAN SECRETORY DDRGK1

(71) Applicant: SHANGHAI NINTH PEOPLE'S HOSPITAL, SHANGHAI JIAOTONG UNIVERSITY SCHOOL OF MEDICINE, Shanghai (CN)

(72) Inventors: Tangjun Zhou, Shanghai (CN); Ying Xia, Shanghai (CN); Xiao Yang, Shanghai (CN); An Qin, Shanghai (CN); Yu Cao, Shanghai (CN); Jie Zhao, Shanghai (CN)

(73) Assignee: SHANGHAI NINTH PEOPLE'S HOSPITAL, SHANGHAI JIAOTONG UNIVERSITY SCHOOL OF MEDICINE, Shanghai (CN)

( * ) Notice: Subject to any disclaimer, the term of this patent is extended or adjusted under 35 U.S.C. 154(b) by 0 days.

(21) Appl. No.: 16/952,391

(22) Filed: Nov. 19, 2020

(65) Prior Publication Data
US 2021/0221860 A1    Jul. 22, 2021

(51) Int. Cl.
C07K 14/47  (2006.01)
A61P 19/00  (2006.01)
A61K 38/00  (2006.01)

(52) U.S. Cl.
CPC .............. *C07K 14/47* (2013.01); *A61P 19/00* (2018.01); *A61K 38/00* (2013.01)

(58) Field of Classification Search
None
See application file for complete search history.

(56) References Cited

PUBLICATIONS

Engusola et al. (J Clin Invest. 2017;127(4):1475-1484) (Year: 2017).*

* cited by examiner

*Primary Examiner* — Sergio Coffa
(74) *Attorney, Agent, or Firm* — Global IP Services; Tianhua Gu

(57) ABSTRACT

The present disclosure provides the use of a recombinant human secretory DDRGK1. Experiments demonstrate that the recombinant human secretory DDRGK1 prepared by the present disclosure can be used in the preparation of biological medicines for treating intervertebral disc degeneration, fractures or bone defects. The recombinant human secretory DDRGK1 of the present disclosure provides a promising direction for the treatment of bone related diseases and has obtained firm scientific evidence, thereby expanding the further application of recombinant human secretory DDRGK1 in clinical practice.

5 Claims, 8 Drawing Sheets
Specification includes a Sequence Listing.

USE OF RECOMBINANT HUMAN SECRETORY DDRGK1

CROSS REFERENCE TO RELATED APPLICATION

This application claims the benefits of priority to Chinese Patent Application No. CN 2019111333468 filed with CNIPA on Nov. 19, 2019, and Chinese Patent Application No. CN 202011294584X filed with CNIPA on Nov. 18, 2020, the contents of which are incorporated herein by reference in its entirety.

BACKGROUND

Field of Disclosure

The present disclosure belongs to the field of treatment of bone and joint diseases, to and in particular, to use of a recombinant human secretory DDRGK1.

Description of Related Arts

China's aging population continues to increase at a rate of 5.2% per year. In 2017, China's population aged 60 or above exceeded 230 million, making it the only country in the world with an elderly population of over 200 million. It is estimated that by 2050, China's aged population will reach 480 million, accounting for about a quarter of the global aged population by then. Health problems related to the aged population increase will also bring a grave challenge to China's medical treatment. Among these health problems, bone and joint diseases (such as osteoarthritis, intervertebral disc degeneration, osteoporosis, and fractures) have an incidence rate of up to 80% in the aged population over 60 years old in China. According to statistics of WHO, the incidence rate of bone and joint diseases ranks second, just behind cardiovascular diseases. At the same time, the high disability rate of bone and joint diseases leads to human resources loss and heavy medical care burden.

At present, the concept of stepped-care has emerged for the treatment of bone and joint diseases, i.e., patients with mild illnesses are treated with drugs. However, for those patients with severe or acute illnesses, it's necessary to adopt invasive surgeries. According to the wound sizes perspective, the invasive surgeries include minimally invasive surgical treatments (such as arthroscopy and TESSYS multiscope) that generally only solve part of the problem, and ultimate surgical treatments (such as joint replacement and intervertebral fusion) that are more traumatic but usually could solve all the disabled problems. For osteoporosis, the prevention and treatment of bone mass can only be improved by using drugs because there is no effective surgical treatment at present.

DDRGK1 consists of 314 amino acids, of which 1-28 is the signal peptide part, which determines whether DDRGK1 is localized in the endoplasmic reticulum or external secretion. DDRGK1 (1-114) may bind to CDK5RAP3 to regulate NF-kB signaling and participate in cell apoptosis induced by endoplasmic reticulum stress (Wu J, Lei G, Mei M, et al. *A novel C53/LZAP-interacting protein regulates stability of C53/LZAP and DDRGK domain-containing Protein 1 (DDRGK1) and modulates NF-kappaB signaling*. The Journal of biological chemistry 2010; 285:15126-36). DDRGK1 (118-216) binds to ASC1 and realizes Ufmylation of ASC1 under the interaction of Ufmylation system proteins, and mediates signal transcription following activation of estrogen receptor α (ERα) (Yoo H M, Kang S H, Kim J Y, et al. *Modification of ASC1 by UFM1 is crucial for ERalpha transactivation and breast cancer development*. Molecular cell 2014; 56:261-74). Lys267 of DDRGK1 binds to UFM1 to form a Lys-Gly covalent cross-linking, so DDRGK1 is also known as UFM1 binding protein (UFBP1) (Tatsumi K, Sou Y S, Tada N, et al. *A novel type of E3 ligase for the Ufm1 conjugation system*. The Journal of biological chemistry 2010; 285:5417-27). Meanwhile, Lys267 of DDRGK1 (216-314) is also a binding site to UFL1, where UFL1 catalyzes the binding of UFM1 to the target protein. The mutation of G at position 408 of DDRGK1 to A may lead to congenital spondyloepiphyseal dysplasia, which may be related to the inhibition of SOX9 ubiquitination-proteasomal degradation by DDRGK1 (Egunsola A T, Bae Y, Jiang M M, et al. *Loss of DDRGK1 modulates SOX9 ubiquitination in spondyloepimetaphyseal dysplasia*. The Journal of clinical investigation 2017; 127:1475-84). It is also found that the binding of DDRGK1 to IkBa may affect the activity of the NF-kB pathway (Xi P, Ding D, Zhou J, et al. *DDRGK1 regulates NF-kappaB activity by modulating IkappaBalpha stability*. PloS one 2013; 8: e64231).

SUMMARY

The present disclosure provides the use of a recombinant human secretory DDRGK1 (containing SEQ ID NO: 2 and SEQ ID NO: 1). Experiments demonstrate that the recombinant human secretory DDRGK1 (containing SEQ ID NO: 2 and SEQ ID NO: 1) prepared by the present disclosure can be used in the preparation of medicines for treating intervertebral disc degeneration, fractures or bone defects. The recombinant human secretory DDRGK1 (containing SEQ ID NO: 2 and SEQ ID NO: 1) of the present disclosure provides a promising direction for the treatment of bone and joint diseases and has obtained firm scientific evidence, thereby expanding the further application of to recombinant human secretory DDRGK1 in clinical practice.

The present disclosure provides the use of a recombinant human secretory DDRGK1 (containing SEQ ID NO: 2 and SEQ ID NO: 1), which is applied to the preparation of medicines for treating bone and joint related diseases.

The recombinant human secretory DDRGK1 (containing SEQ ID NO: 2 and SEQ ID NO: 1) is a DDRGK1 protein with sites 1-28 removed and transforms from a protein located in cell membrane to a secretory-type protein.

Further, the recombinant human secretory DDRGK1 (containing SEQ ID NO: 2 and SEQ ID NO: 1) can promote the formation of disulfide bond of extracellular matrix protein by inhibiting reactive oxygen species (ROS) in nucleus pulposus cells, and ultimately facilitate the repair of nucleus pulposus and intervertebral disc.

Further, the recombinant human secretory DDRGK1 (containing SEQ ID NO: 2 and SEQ ID NO: 1) promotes the osteogenic ability of bone marrow mesenchymal stem cells.

The recombinant human secretory DDRGK1 (containing SEQ ID NO: 2 and SEQ ID NO: 1) may be used to prepare a medicine for treating intervertebral disc degeneration or osteoporosis.

The recombinant human secretory DDRGK1 (containing SEQ ID NO: 2 and SEQ ID NO: 1) may be used to prepare a medicine for treating fractures or bone defects.

The medicine takes the recombinant human secretory DDRGK1 (containing SEQ ID NO: 2 and SEQ ID NO: 1) as an active ingredient, and is prepared into preparation for use with pharmaceutically acceptable excipients or auxiliary ingredients.

The preparation is selected from one of injection, subcutaneous implant, tablet, powder, granule, capsule, oral liquid, and slow-released formulation.

Beneficial Effect:

Experiments demonstrate that the synthesis of the recombinant human secretory DDRGK1 (containing SEQ ID NO: 2 and SEQ ID NO: 1), together with its application in the preparation of medicines for treating intervertebral disc degeneration, fractures or bone to defects, provide a promising direction for the treatment of bone and joint diseases and have obtained firm scientific evidence, thereby expanding further applications of the recombinant human secretory DDRGK1 in clinical practice.

BRIEF DESCRIPTION OF THE DRAWINGS

The upper diagram of FIG. 10 shows the microscopic view (left) and general view (right) of ALP staining result of m-BMSC after 7 days and 14 days of osteogenic differentiation culture under the treatment of recombinant human secretory DDRGK1 (containing SEQ ID NO: 2 and SEQ ID NO: 1); the lower diagram of FIG. 10 shows the general view (left) and microscopic view (right) of alizarin red staining result of m-BMSC after 21 days of osteogenic differentiation culture under the treatment of recombinant human secretory DDRGK1 (containing SEQ ID NO: 2 and SEQ ID NO: 1)

The left diagram of FIG. 11 shows the general view of ALP staining result of h-BMSC after 7 days and 14 days of osteogenic differentiation culture under the treatment of recombinant human secretory DDRGK1 (containing SEQ ID NO: 2 and SEQ ID NO: 1); the right diagram of FIG. 11 shows the general view (left) and microscopic view (right) of alizarin red staining result of h-BMSC after 21 days of osteogenic differentiation culture under the treatment of recombinant human secretory DDRGK1 (containing SEQ ID NO: 2 and SEQ ID NO: 1)

The upper diagram of FIG. 12 shows the general view of ALP staining result of MC3T3-E1 after 7 days and 14 days of osteogenic differentiation culture under the treatment of recombinant human secretory DDRGK1 (containing SEQ ID NO: 2 and SEQ ID NO: 1); the lower diagram of FIG. 12 shows the microscopic view (left) and general view (right) of alizarin red staining result of MC3T3-E1 after 21 days of osteogenic differentiation culture under the treatment of recombinant human secretory DDRGK1 (containing SEQ ID NO: 2 and SEQ ID NO: 1)

DETAILED DESCRIPTION OF THE PREFERRED EMBODIMENTS

The present disclosure will be further described below with reference to specific embodiments. It should be understood that the embodiments are just for describing the present disclosure instead of limiting the scope of the present disclosure. In addition, it should be understood that after reading the teachings of the present disclosure, various changes or modifications to the present disclosure may be made by the skilled in the art, and these equivalent forms fall within the scope defined by the appended claims of the present disclosure.

Embodiment 1

1. Experimental Materials

Human DDRGK1 gene (synthesized by Genewiz Biotechnology Co., Ltd and subjected to codon optimization for humans).

Expi293F cells (Thermo Fisher, A14527).

pcDNA3.4-HHC plasmid (modified by Cao Yu's research group, Institute of Precision Medicine, Shanghai Ninth People's Hospital, Shanghai Jiaotong University School of Medicine).

Molecular exclusion chromatography column (GE, Superdex 200 Increase 10/300 GL).

Ni Smart Beads 6FF affinity chromatography medium (Smart-Lifesciences, SA036100).

Tobacco etch virus protease TEV (recombined and expressed by Cao Yu's research group, Institute of Precision Medicine, Shanghai Ninth People's Hospital, Shanghai Jiaotong University School of Medicine).

SPINX centrifugal filter (Bioscience Technology Co. Ltd).

Rat bone marrow mesenchymal stem cells BMSC (Shanghai Key Laboratory of Orthopaedic Implants, Shanghai Ninth People's Hospital, Shanghai Jiaotong University School of Medicine).

293 cell culture medium (Union-biotech Co., Ltd., UP0050).

Transfection reagent PEI MAX (Polyscience, 24765).

Rat nucleus pulposus cells (Shanghai Key Laboratory of Orthopaedic Implants, Shanghai Ninth People's Hospital, Shanghai Jiaotong University School of Medicine).

ITS-F12 culture medium (Shanghai Key Laboratory of Orthopaedic Implants, Shanghai Ninth People's Hospital, Shanghai Jiaotong University School of Medicine).

Mouse bone marrow mesenchymal stem cells m-BMSC (Shanghai Key Laboratory of Orthopaedic Implants, Shanghai Ninth People's Hospital, Shanghai Jiaotong University School of Medicine).

Human bone marrow mesenchymal stem cells h-BMSC (Shanghai Key Laboratory of Orthopaedic Implants, Shanghai Ninth People's Hospital, Shanghai Jiaotong University School of Medicine).

Mouse MC3T3-E1 cell line (Shanghai Key Laboratory of Orthopaedic Implants, Shanghai Ninth People's Hospital, Shanghai Jiaotong University School of Medicine).

Figure 1:
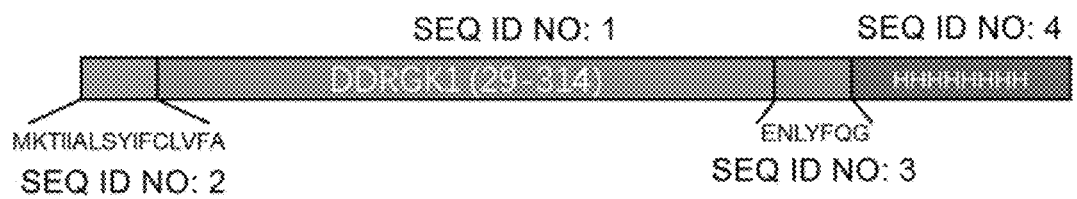
FIG. 1 is a schematic diagram of the DDRGK1 expression construct (containing SEQ ID NO: 2, SEQ ID NO: 1, SEQ ID NO: 3 and SEQ ID NO: 4).

2. Experimental Method 2.1 Construction of Recombinant Expression Vector and Expression of the Target Protein The human DDRGK1 gene (NCBI reference sequence: NM_023935.2) is synthesized by Genewiz Biotechnology Co., Ltd after codon optimization. As shown in FIG. 1, a truncated human DDRGK1 cDNA fragment encoding amino acid residues in which positions 1-28 are deleted is obtained by PCR (corresponding to the following amino acids sequence: AS AGQEPLHNEE LAGAGRVAQP GPLEPEEPRA GGRPRRRRDL GSRLQAQRRA QRVAWAEADE NEEEAVILAQ EEEGVEKPAE THLSGKIGAK KLRKLEEKQA RKAQREAEEA EREERKRLES QREAEWKKEE ERLRLEEEQK EEEERKAREE QAQREHEEYL KLKEAFVVEE EGVGETMTEE QSQSFLTEFI NYIKQSKVVL LEDLASQVGL RTQDTINRIQ DLLAEGTITG VIDDRGKFIY ITPEELAAVA NFIRQRGRVS IAELAQASNS LIAWGRESPA QAPA (SEQ ID NO: 1)). The fragment is cloned into a lab-modified pCDNA3.4 plasmid after being double-digested by AscI/NotI. The N-terminal of the gene sequence is connected with a membrane-spanning signal peptide MKTIIALSYIFCLVFA (SEQ ID NO: 2), and the C-terminal is connected with a TEV restriction enzyme cutting site ENLYFQG (SEQ ID NO: 3) and a purification tag HHHHHHHH (SEQ ID NO: 4).

Expi293F cells are cultured in suspension under the conditions of 37° C., 110 rpm and 5% $CO_2$, and are transfected when the number of cells reached a density of $2.5\times10^6$ per ml. 1 mg of expression plasmid DNA is used to transfect 1 L cells. The expression plasmid and transfection reagent PEI MAX are pre-mixed in 100 mL fresh culture medium at a ratio of 1:3 (w/w), incubated for 30 min, then totally added into 1 L Expi293F cells for suspension culture under the original conditions. After 72 hours of transfection, the cell culture supernatant is collected for protein purification 2.2 Protein Purification The cell culture is centrifuged at 1500 g for 10 minutes to collect the supernatant. The obtained supernatant is centrifuged at 5000 g for 20 minutes to collect the supernatant. 2 mL of Ni Smart Beads 6FF purification medium is loaded into the purification empty column. Firstly, the purification medium is washed with deionized water of about 20 column volumes. Then, the purification medium is pre-equilibrated with buffer (20 mM Hepes pH 8.0, 150 mM NaCl, 10% Glycerol) of about 20 column volumes. Thereafter, the supernatant is loaded into the pre-equilibrated purification medium at a flow rate of about 0.5 ml/min. After the supernatant has completely flowed through, the purification medium is washed with a buffer of about 20 column volumes. Finally, the medium is resuspended into a centrifuge tube with a buffer of about 3 column volumes, and about 0.4 mg of TEV protease is added to the medium. The medium is placed on a rotary shaker and enzyme-digested overnight at 4□.

Figure 2:
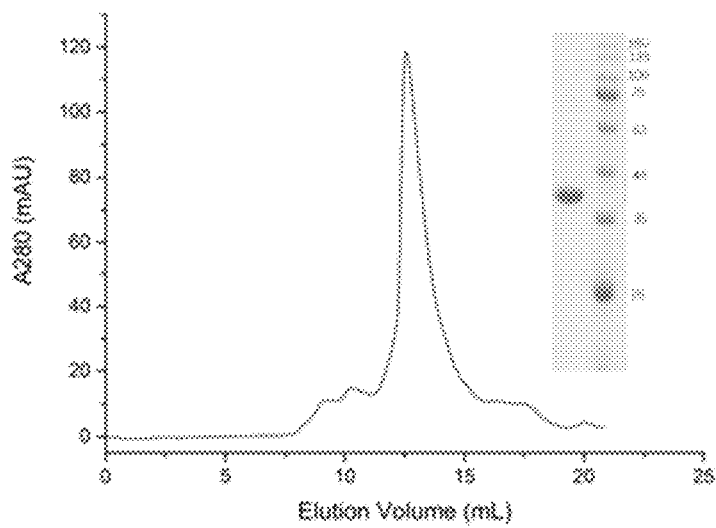
FIG. 2 is a molecular exclusion chromatogram of DDRGK1.

The sample digested overnight in the centrifuge tube is re-loaded into an empty purification column container and the digested flow-through fluid is collected. Then, a buffer of about two column volumes is divided into two parts, which slowly flow through the purification medium; the flow-through fluid is collected. Finally, all the flow-through fluid is combined. The combined flow-through fluid is concentrated to 1 ml, and the sample is filtered using a SPINX centrifugal filter. Then, the sample is further subjected to separation and purification by a molecular exclusion chromatography column (Superdex 200 Increase 10/300 GL, GE Healthcare), as shown in FIG. 2. The molecular exclusion chromatography column is pre-installed on the AKTA PURE instrument at 4° C. and pre-equilibrated with 20 mM Hepes pH 8.0, 150 mM NaCl as the mobile phase. After checking the purity of the protein by SDS-PAGE, the fraction containing DDRGK1 protein (the protein peak position corresponding to fplc) is collected for subsequent experiments.

2.3 IVF Mice with DDRGK1 (Positions 1-28 being Knockout) Under the CRISPR/Cas9 System are Constructed According to Conventional Methods in the Field.

2.4 Osteogenic Differentiation

SD rat and C57BL/6 mouse bone marrow mesenchymal stem cell osteogenic differentiation medium kit (Cyagen) are used. According to the requirements of the kit, SD rat and C57BL/6 mouse bone marrow mesenchymal stem cell osteogenic induced differentiation complete culture medium is prepared. The surface of the culture well plates is coated with 0.1% gelatin. The SD rat and C57BL/6 mouse bone marrow mesenchymal stem cells are inoculated into the well plates at a density of $2\times10^4$ cells/$cm^2$. The to osteogenic induced differentiation complete culture medium is added, and different concentrations of recombinant human secretory DDRGK1 (containing SEQ ID NO: 2 and SEQ ID NO: 1) are given. The medium is changed with fresh osteogenic induced differentiation medium every 3 days. After 7 weeks of induction, ALP staining is performed. After 14 weeks of induction, Alcian blue staining is performed.

2.5 Chondrogenic Differentiation

ITS-F12 culture medium is used. 10 ul of mouse primary chondrocytes and SD rat nucleus pulposus cells are inoculated into well plates at $1.5\times10^7$ cells/ml. ITS-F12 culture medium is added, and different concentrations of recombinant human secretory DDRGK1 (containing SEQ ID NO: 2 and SEQ ID NO: 1) are given. The ITS-F12 culture medium is changed every 3 days. After 9 days of induction, Alcian blue staining result is performed.

2.6 Detection of Reactive Oxygen Species by DCFH Method

A proper amount of cells are inoculated into the well plates. DCFH-DA is diluted with serum-free culture medium at a ratio of 1:1000 to a final concentration of 10 µmol/L.

The cell culture medium is removed, and a proper volume of diluted DCFH-DA is added. The volume of the added diluted DCFH-DA should be sufficient to cover the cells. Usually, at least 1 ml of diluted DCFH-DA is added to one well of the six-well plate. After incubating in a cell incubator at 37° C. for 20 min, the cells are washed with a serum-free cell culture medium for three times to sufficiently remove the DCFH-DA that did not enter into the cells. After adding hydrogen peroxide for 5 minutes, and then being rescued by 2 ug recombinant human secretory DDRGK1 (containing SEQ ID NO: 2 and SEQ ID NO: 1) for 25 minutes, the cells are observed under green fluorescence scope.

2.7 Repair Model of Tibia Defect and Skull Defect in Mice

Eight-week C57 male mice are used to carry out the tibia defect model: after anesthesia, the mice are maintained at a supine position to depilate the right lower limb and be disinfected with alcohol or iodophor cotton balls for three times; the knee joint serves as the anatomic landmark, the skin above the knee joint is cut open with a sterile scalpel or a scissor to expose the ligamentum patellae of the mice; at 0.5 cm below the tibial plateau, the joint position between the lower edge of ligamentum patellae and the tibial tuberosity is cut open toward the medial side for 2 mm, and the muscle is cut with a sterile blade to expose the medial bone surface of the tibia; first, a 5 ml syringe needle is used to make a hole, the hole is then drilled to a proper diameter using a conical abrasion drill, and finally, the diameter of the hole is determined to be 1 mm by using a 1 mm-diameter cylindrical abrasion drill. After the operation, the skin is directly sutured without suturing the muscle, and iodophor is used for disinfection. The mice are divided into 4 groups (group A: 100 ul lysis buffer for each mouse per time; group B: 2500 ng DDRGK1 dissolved in 100 ul lysis buffer for each mouse per time; group C: 2500 ng denatured DDRGK1 dissolved in 100 ul lysis buffer (under metal bath at 99° C. for 5 min) for each mouse per time; group D: 250 ng BMP2 dissolved in 100 ul lysis buffer for each mouse per time). On the $2^{nd}$, $4^{th}$ $6^{th}$ and $8^{th}$ day after the operation, local administration is given to the operative sites. On the $10^{th}$ day after the operation, the samples are obtained from the right lower limbs and fixed in paraformaldehyde.

Eight-week C57 male mice are used to carry out the skull defect model: after anesthesia, the mice are maintained at a prone position to depilate the scalp and be disinfected with alcohol or iodophor cotton balls for three times; the skull vertice serves as the anatomic landmark, the skin above the skull is cut open with a sterile scalpel or a scissor to expose the skull of the mice; a 2 mm incision is made next to the middle suture of the skull; first, a 5 ml syringe needle is used to make a hole, the hole is then drilled to a proper diameter using a conical abrasion drill, and finally, the diameter of the hole is determined to be 1 mm by using a 1 mm-diameter cylindrical abrasion drill. After the operation, the skin is directly sutured, and iodophor is used for disinfection. The mice are divided into 2 groups (control group: 100 ul lysis buffer for each mouse per time; DDRGK1 group: 2500 ng DDRGK1 dissolved in 100 ul lysis buffer for each mouse per time). On the $2^{nd}$, $4^{th}$, $6^{th}$ and $8^{th}$ day after the operation, local administration is given to the operative sites. On the $10^{th}$ day after the operation, the samples are obtained from the skulls and fixed in paraformaldehyde.

2.8 DTNB, β-ME, and Tert-Butyl Hydroperoxide Method

DTNB (10 mM), β-ME (20 mM), and tert-butyl hydrogen peroxide (7%) are prepared at room temperature. DTNB and β-ME are mixed in a ratio of 2:1. A standard curve is made using a 96-well plate (100 ul per well), and a microplate reader for measuring absorbable light at a wavelength of 405 nm. 2 mM-SH and 30 ug/ml recombinant human secretory DDRGK1 (containing SEQ ID NO: 2 and SEQ ID NO: 1), total volume of 90 ul) are spotted on the 96-well plate. After 10 ul tert-butyl hydroperoxide (7%) is added, the measurement is immediately performed with the microplate reader, once every 1 minute. A concentration-time diagram is drawn.

Figure 3:
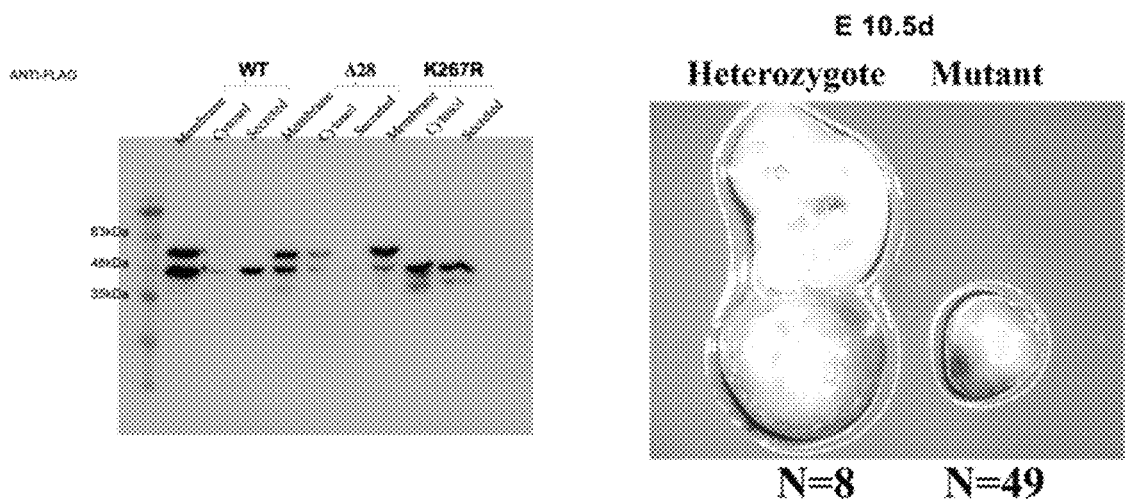
FIG. 3 shows the reduction of protein exocrine after the excision of sites 1-28 of the wild-type DDRGK1 (left), while the mouse embryogenesis is depressed (right).

3. Experimental Results 3.1 Discovery of Recombinant Human Secretory DDRGK1 (Containing SEQ ID NO: 2 and SEQ ID NO: 1) and its Effect on Mouse Embryos As shown in the left part of FIG. 3, wild-type (WT) DDRGK1 exhibits secretory type and membrane type (lanes 2, 3 and 4); No. 1-28 excised DDRGK1 has increased intracellular expression (lane 6) and reduced secretory type (lane 7). K267R mutation appears to increase intracellular expression (lane 9). As shown in the right part of FIG. 3, due to the removal of 1-28 sites, DDRGK1 cannot be secreted and mouse embryogenesis is depressed.

Figure 4:
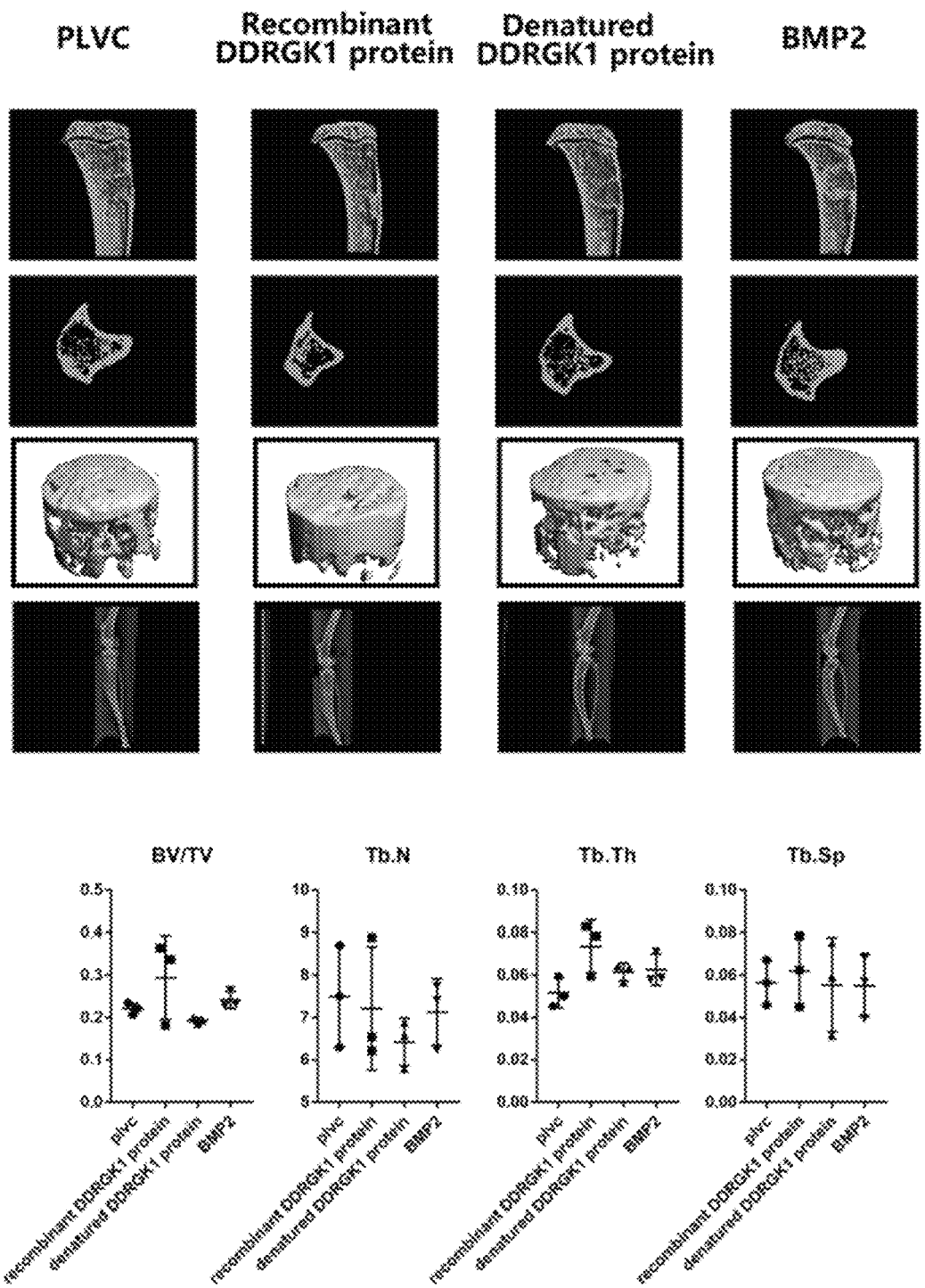
FIG. 4 shows the repair of mouse tibia defect model by recombinant human secretory DDRGK1 (containing SEQ ID NO: 2 and SEQ ID NO: 1).

3.2 Repair Effect of Recombinant Human Secretory DDRGK1 (Containing SEQ ID NO: 2 and SEQ ID NO: 1) on Tibial Bone Defect in Rats It can be seen from FIG. 4 that the repair of tibial bone defect in rats in the recombinant human secretory DDRGK1 group was significantly better than that in control group, denatured recombinant human secretory DDRGK1 group and BMP 2 group. The BV/TV ratio of the recombinant human secretory DDRGK1 group was significantly higher than those of other groups.

The result indicates that the recombinant human secretory DDRGK1 (containing SEQ ID NO: 2 and SEQ ID NO: 1) can promote the repair of tibial bone defects in rats.

3.3 Effect of Recombinant Human Secretory DDRGK1 (Containing SEQ ID NO: 2 and SEQ ID NO: 1) on Osteogenic Differentiation of Rat Bone Marrow Mesenchymal Stem Cells (BMSCs)

Figure 5:
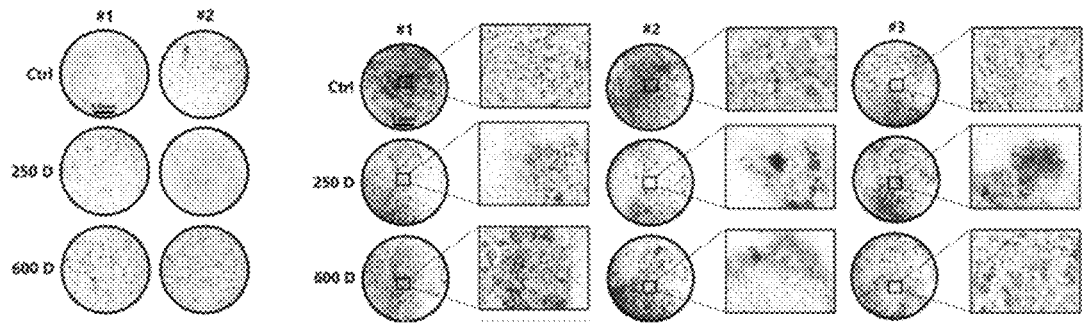
FIG. 5 shows the ALP staining result on the $7^{th}$ day after recombinant human secretory DDRGK1 (250 ng and 600 ng) stimulating rat BMSC cells and inducing osteogenesis (left), and the alizarin red staining result on the 14th day after recombinant human secretory DDRGK1 (250 ng and 600 ng) stimulating rat BMSC cells (right).

As shown in the left part of FIG. 5, the ALP staining result of BMSC under the treatment of recombinant human secretory DDRGK1 (containing SEQ ID NO: 2 and SEQ ID NO: 1) was significantly increased compared with the control group. As shown in the right part of FIG. 5, the alizarin red staining result of BMSC under the treatment of recombinant human secretory DDRGK1 (containing SEQ ID NO: 2 and SEQ ID NO: 1) was significantly increased compared with the control group.

The results show that recombinant human secretory DDRGK1 (containing SEQ ID NO: 2 and SEQ ID NO: 1) is capable of improving the osteogenic differentiation of rat bone marrow mesenchymal stem cells (BMSCs).

Figure 6:
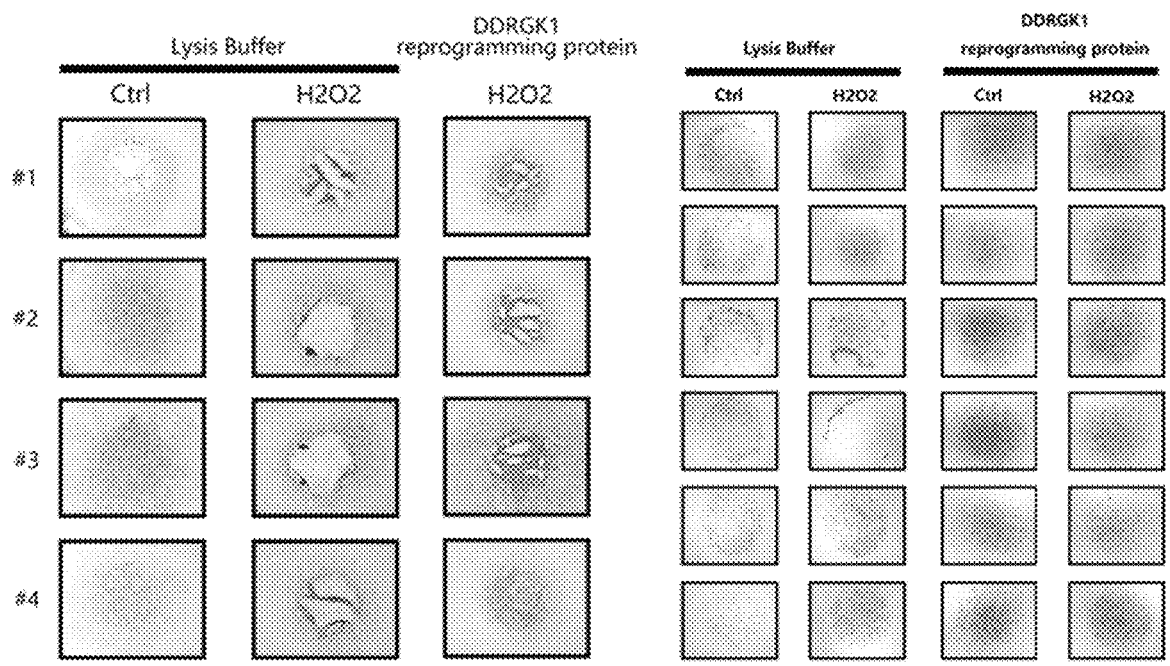
FIG. 6 shows the alcian blue staining result on the $21^{st}$ day of high-density culture after the rat nucleus pulposus primary cells are rescued by 2 ug of recombinant human secretory DDRGK1 (containing SEQ ID NO: 2 and SEQ ID NO: 1) under ROS stress.

3.4 Effect of Recombinant Human Secretory DDRGK1 (Containing SEQ ID NO: 2 and SEQ ID NO: 1) on Rescuing Oxidative Stress (ROS) in Rat Nucleus Pulposus Primary Cells It can be seen from FIG. 6 that under ROS stimulation, recombinant human secretory DDRGK1 (containing SEQ ID NO: 2 and SEQ ID NO: 1) significantly improves the Alcian blue staining result of mouse primary chondrocytes and rat nucleus pulposus primary cells, compared with the control group. Under the treatment of recombinant human secretory DDRGK1 (containing SEQ ID NO: 2 and SEQ ID NO: 1), chondrocytes and nucleus pulposus cells were more resistant to ROS and had the same amount of extracellular matrix as the ROS-free group.

The result indicates that recombinant human secretory DDRGK1 (containing SEQ ID NO: 2 and SEQ ID NO: 1) can promote the resistance of rat nucleus pulposus cells to ROS.

Figure 7:
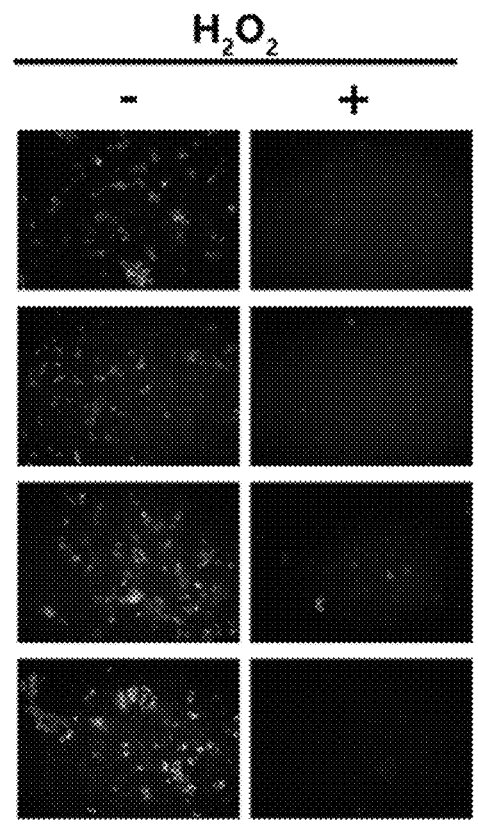
FIG. 7 shows the detection of reactive oxygen species by DCFH method after the rat nucleus pulposus primary cells are rescued by 2 ug of recombinant human secretory DDRGK1 (containing SEQ ID NO: 2 and SEQ ID NO: 1) under ROS stress.

3.5 Detection of Intracellular Reactive Oxygen Species (ROS) Under the Treatment of Recombinant Human Secretory DDRGK1 (Containing SEQ ID NO: 2 and SEQ ID NO: 1) on to Rat Primary Nucleus Pulposus Cells The rat primary nucleus pulposus cells with high ROS were constructed with hydrogen peroxide and rescued with recombinant human secretory DDRGK1 (containing SEQ ID NO: 2 and SEQ ID NO: 1). It can be seen from FIG. 7 that the green fluorescence of DCFH in the recombinant human secretory DDRGK1 rescue group is significantly lower than that in the ROS stress group.

The result indicates that the recombinant human secretory DDRGK1 (containing SEQ ID NO: 2 and SEQ ID NO: 1) antagonizes ROS by scavenging reactive oxygen species in rat primary nucleus pulposus cells.

3.6 Promotion Effect of Recombinant Human Secretory DDRGK1 (Containing SEQ ID NO: 2 and SEQ ID NO: 1) on the Formation of Disulfide Bond The half-reaction time of disulfide bond formation after using recombinant human secretory DDRGK1 (containing SEQ ID NO: 2 and SEQ ID NO: 1) is significantly lower than that of the control group.

Figure 8:
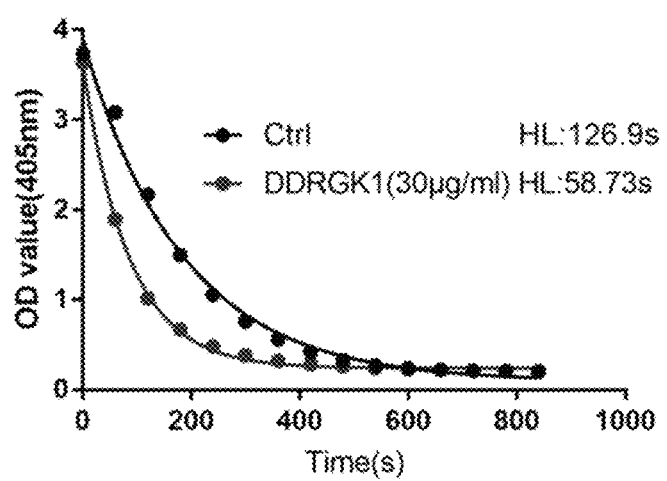
FIG. 8 shows the detection of promotion of disulfide bond formation by 30 ug/ml recombinant human secretory DDRGK1 (containing SEQ ID NO: 2 and SEQ ID NO: 1) using DTNB, β-ME, and tert-butyl hydroperoxide method.

It can be seen from FIG. 8 that recombinant human secretory DDRGK1 (containing SEQ ID NO: 2 and SEQ ID NO: 1) promotes the formation of disulfide bonds, thereby resisting the degradation of the nucleus pulposus extracellular matrix caused by oxidative stress, thereby repairing the intervertebral disc.

Figure 9:
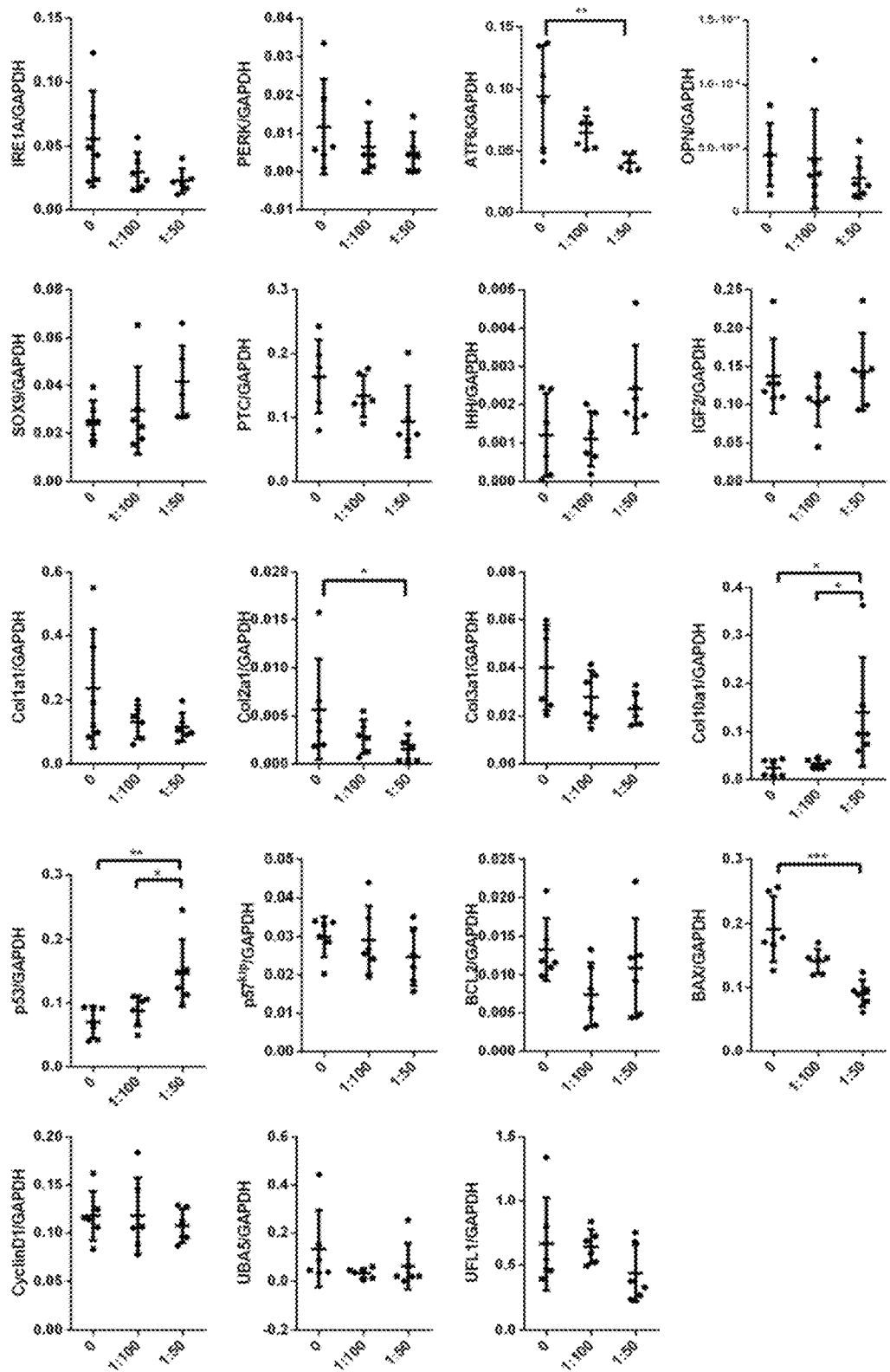
FIG. 9 shows the effect of recombinant human secretory DDRGK1 (containing SEQ to ID NO: 2 and SEQ ID NO: 1) on ATDC5 soft cell line.

3.7 Effect of Recombinant Human Secretory DDRGK1 (Containing SEQ ID NO: 2 and SEQ ID NO: 1) on ATDC5 Soft Cell Line ATDC5 (pre-proliferative chondrocytes, which can be induced to differentiate into proliferative chondrocytes, hypertrophic chondrocytes, and eventually bones) was treated with secretory DDRGK1 recombinant protein for 96 hours, and PCR was carried out (without ITS differentiation culture). As shown in FIG. 9:

a. the endoplasmic reticulum stress pathway (ER-Stress pathway) is inhibited;

b. the cartilage differentiation maker SOX9 may increase;

c. PTC (proliferative chondrocyte maker) decreases;

d. IHH (maker of pre-hypertrophic chondrocytes and hypertrophic chondrocytes) increases;

e. OPN expression is too low and no osteogenic differentiation is observed;

f. Col10a1 (maker of hypertrophic chondrocytes) increases;

g. p53 (proliferation maker) increases;

h. BAX (apoptosis maker) decreases.

The result indicates that the secretory DDRGK1 induces ATDC5 to differentiate into hypertrophic chondrocytes via the ER-Stress pathway (a longer induction may induce terminal differentiation and eventually lead to the formation of bones).

3.8 Effect of Recombinant Human Secretory DDRGK1 (Containing SEQ ID NO: 2 and SEQ ID NO: 1) on Osteogenic Differentiation of Mouse Bone Marrow Mesenchymal Stem Cells (m-BMSCs)

Figure 10:
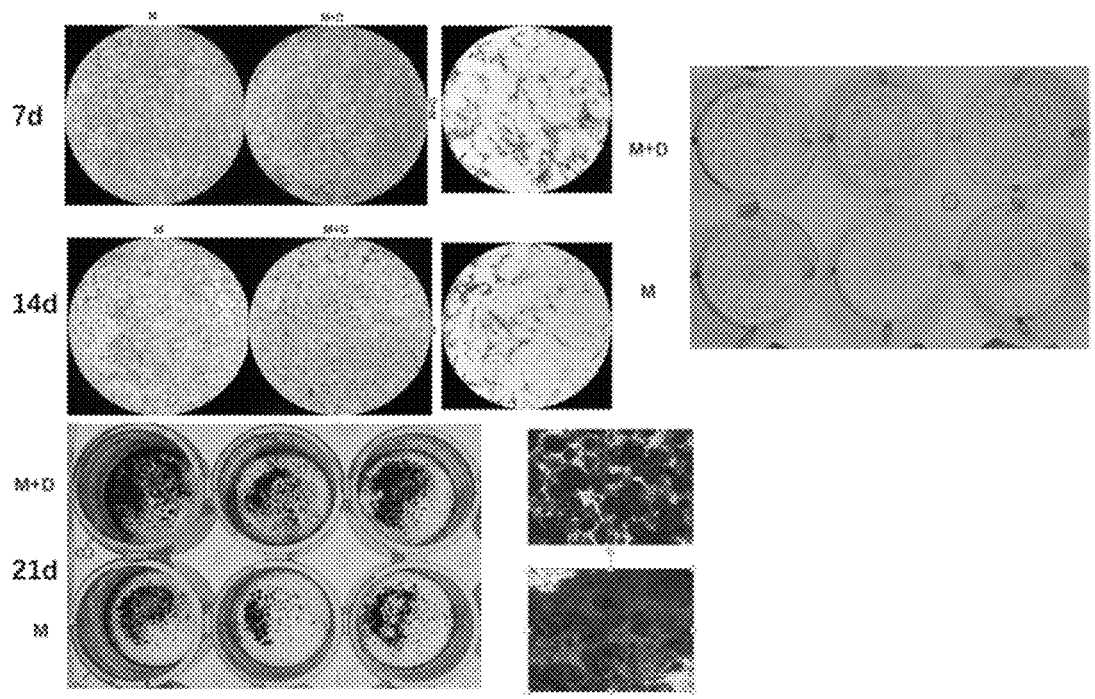
in FIG. 10, M+D refers to m-BMSC+recombinant human secretory DDRGK1 (containing SEQ ID NO: 2 and SEQ ID NO: 1); M refers to m-BMSC.

As shown in the upper part of FIG. 10, the ALP staining result of m-BMSC under the treatment of recombinant human secretory DDRGK1 (containing SEQ ID NO: 2 and SEQ ID NO: 1) was significantly increased compared with the control group. As shown in the lower part of FIG. 10, the alizarin red staining result of m-BMSC under the treatment of recombinant human secretory DDRGK1 (containing SEQ ID NO: 2 and SEQ ID NO: 1) was significantly increased compared with the control group.

The results show that recombinant human secretory DDRGK1 (containing SEQ ID NO: 2 and SEQ ID NO: 1) is capable of improving the osteogenic differentiation of mouse bone marrow mesenchymal stem cells (m-BMSCs).

3.9 Effect of Recombinant Human Secretory DDRGK1 (Containing SEQ ID NO: 2 and SEQ to ID NO: 1) on Osteogenic Differentiation of Human Bone Marrow Mesenchymal Stem Cells (h-BMSCs)

Figure 11:
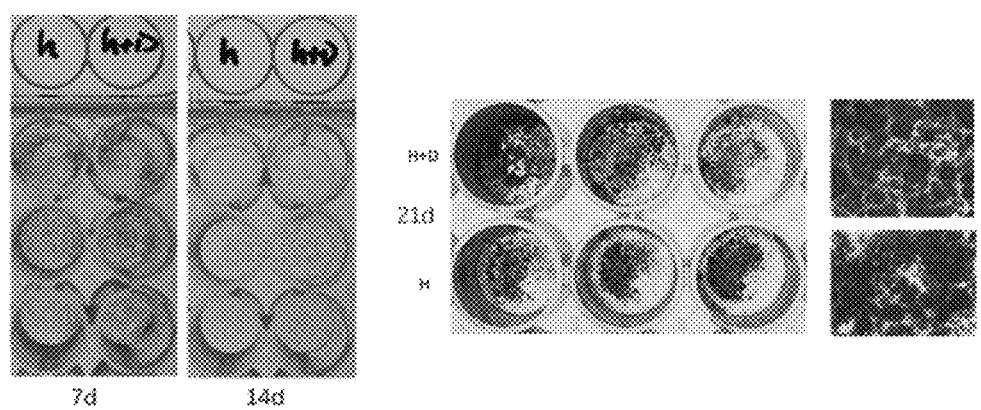
in FIG. 11, H+D refers to h-BMSC+recombinant human secretory DDRGK1; H refers to h-BMSC.

As shown in the left part of FIG. 11, the ALP staining result of h-BMSC under the treatment of recombinant human secretory DDRGK1 (containing SEQ ID NO: 2 and SEQ ID NO: 1) was significantly increased compared with the control group. As shown in the right part of FIG. 11, the alizarin red staining result of h-BMSC under the treatment of recombinant human secretory DDRGK1 (containing SEQ ID NO: 2 and SEQ ID NO: 1) was significantly increased compared with the control group.

The results show that recombinant human secretory DDRGK1 (containing SEQ ID NO: 2 and SEQ ID NO: 1) is capable of improving the osteogenic differentiation of human bone marrow mesenchymal stem cells (h-BMSCs).

Figure 12:
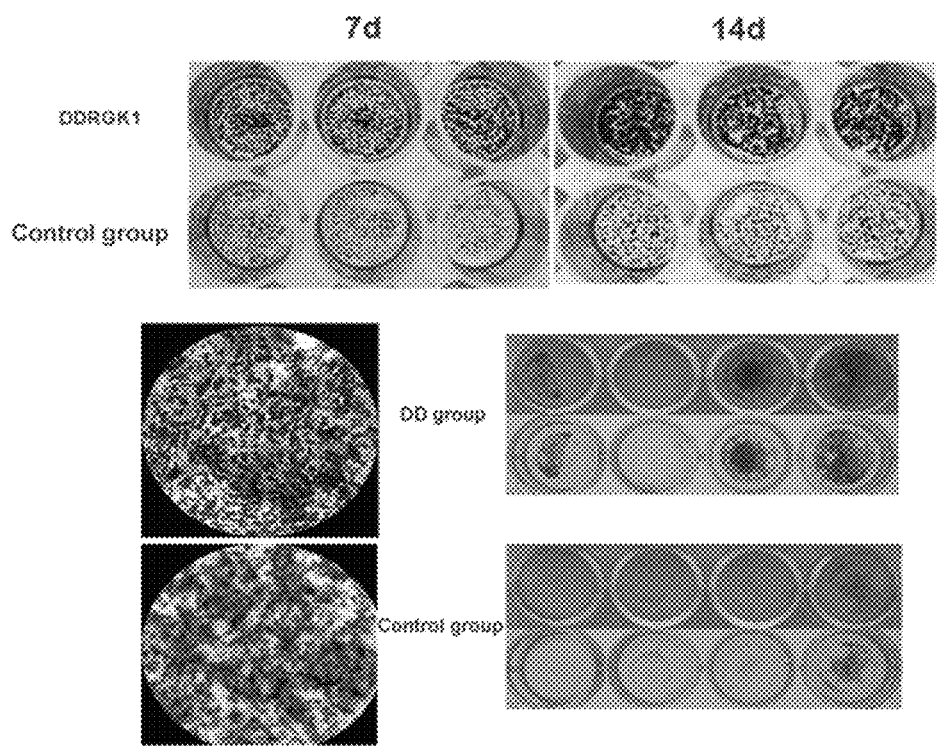
in FIG. 12, DDRGK1 refers to MC3T3-E1+recombinant human secretory DDRGK1 (containing SEQ ID NO: 2 and SEQ ID NO: 1); control group refers to MC3T3-E1.

3.10 Effect of Recombinant Human Secretory DDRGK1 (Containing SEQ ID NO: 2 and SEQ ID NO: 1) on Osteogenic Differentiation of Mouse MC3T3-E1 Cell Line As shown in the upper part of FIG. 12, the ALP staining result of MC3T3-E1 under the treatment of recombinant human secretory DDRGK1 (containing SEQ ID NO: 2 and SEQ ID NO: 1) was significantly increased compared with the control group. As shown in the lower part of FIG. 12, the alizarin red staining result of MC3T3-E1 under the treatment of recombinant human secretory DDRGK1 (containing SEQ ID NO: 2 and SEQ ID NO: 1) was significantly increased compared with the control group.

The results show that recombinant human secretory DDRGK1 (containing SEQ ID NO: 2 and SEQ ID NO: 1) is capable of improving the osteogenic differentiation of mouse MC3T3-E1.

Figure 13:
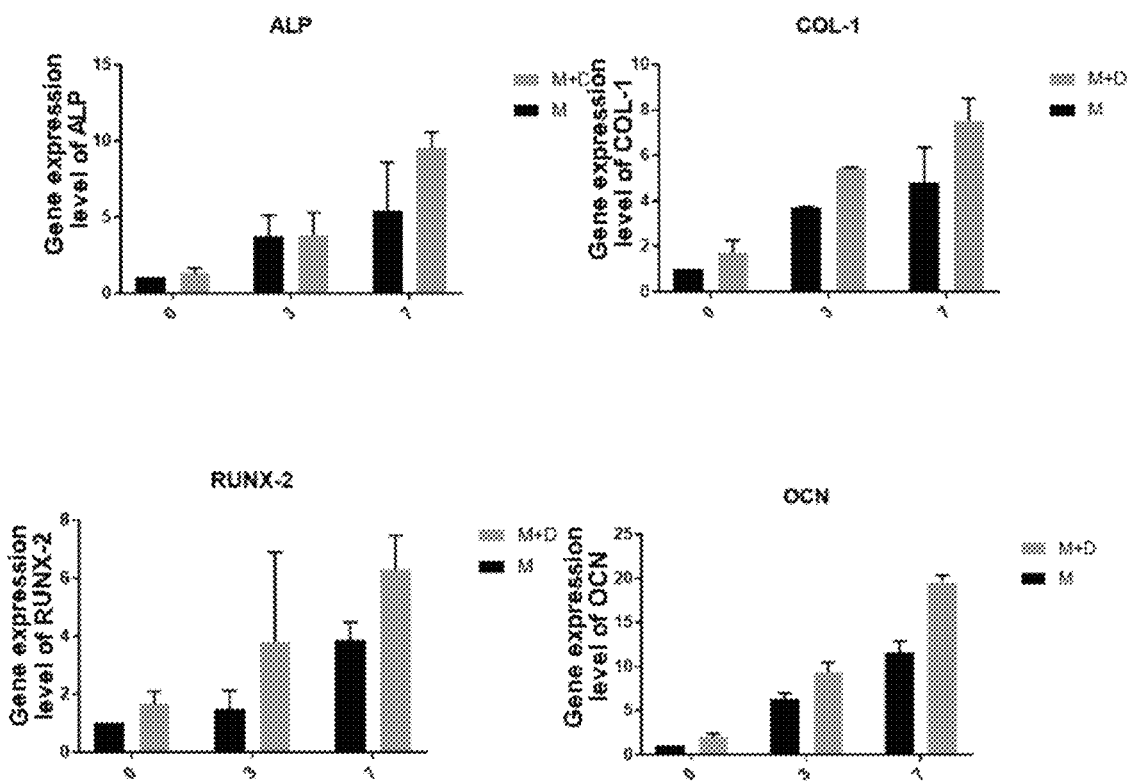
FIG. 13 shows PCR detection of osteogenesis marker mRNA of mouse bone marrow mesenchymal stem cells (m-BMSCs) under the treatment of recombinant human secretory DDRGK1 (containing SEQ ID NO: 2 and SEQ ID NO: 1).

3.11 PCR Detection of Osteogenesis Marker mRNA of Mouse Bone Marrow Mesenchymal Stem Cells (m-BMSCs) Under the Treatment of Recombinant Human Secretory DDRGK1 (Containing SEQ ID NO: 2 and SEQ ID NO: 1)

m-BMSC was treated with recombinant human secretory DDRGK1 recombinant protein (containing SEQ ID NO: 2 and SEQ ID NO: 1) for 0, 3, and 7 days, and PCR was to carried out. As shown in FIG. 13:

On the $7^{th}$ day of stimulation, the ALP of m-BMSC increased significantly under the treatment of recombinant human secretory DDRGK1 (containing SEQ ID NO: 2 and SEQ ID NO: 1);

On the $7^{th}$ day of stimulation, the Col-1 of m-BMSC increased significantly under the treatment of recombinant human secretory DDRGK1 (containing SEQ ID NO: 2 and SEQ ID NO: 1);

On the $7^{th}$ day of stimulation, the RUNX-2 of m-BMSC increased significantly under the treatment of recombinant human secretory DDRGK1 (containing SEQ ID NO: 2 and SEQ ID NO: 1);

On the $7^{th}$ day of stimulation, the OCN of m-BMSC increased significantly under the treatment of recombinant human secretory DDRGK1 (containing SEQ ID NO: 2 and SEQ ID NO: 1).

The results show that recombinant human secretory DDRGK1 (containing SEQ ID NO: 2 and SEQ ID NO: 1) is capable of improving the expression of the osteogenic differentiation marker mRNA of mouse bone marrow mesenchymal stem cells (m-BMSCs).

Figure 14:
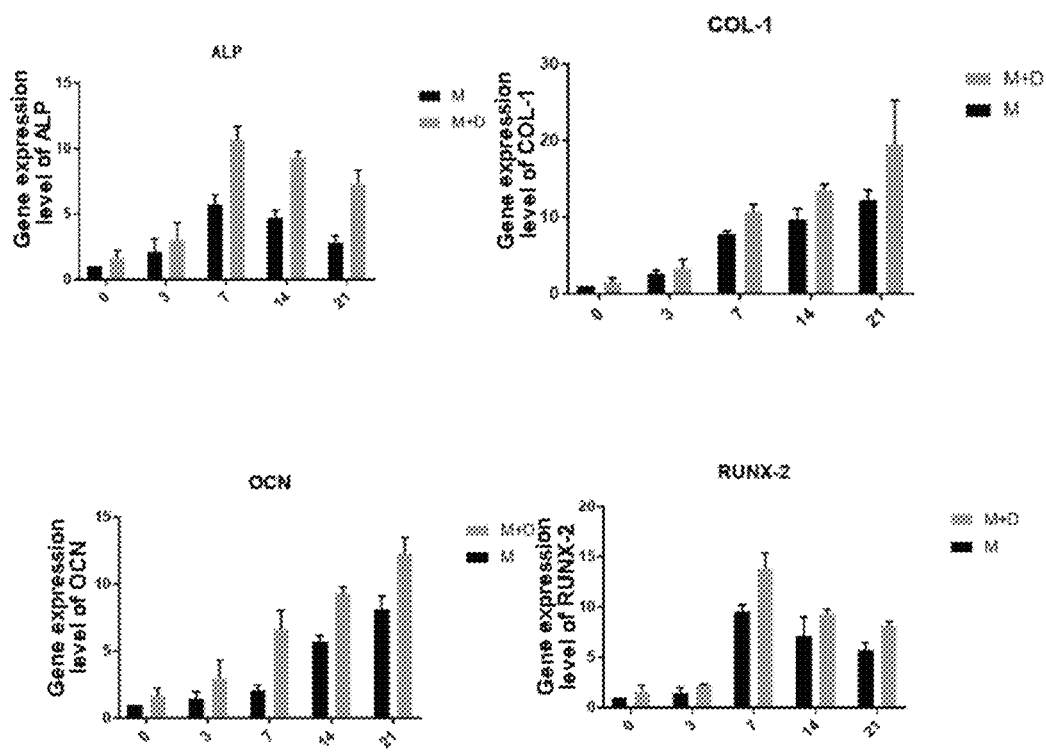
FIG. 14 shows PCR detection of osteogenesis marker mRNA of mouse MC3T3-E1 cell line under the treatment of recombinant human secretory DDRGK1 (containing SEQ ID NO: 2 and SEQ ID NO: 1).

3.12 PCR Detection of Osteogenesis Marker mRNA of Mouse MC3T3-E1 Cell Line Under the Treatment of Recombinant Human Secretory DDRGK1 (Containing SEQ ID NO: 2 and SEQ ID NO: 1)

m-BMSC was treated with recombinant human secretory DDRGK1 recombinant protein (containing SEQ ID NO: 2 and SEQ ID NO: 1) for 0, 3, 7, 14, and 21 days, and PCR was carried out. As shown in FIG. 14:

On the 7$^{th}$ day of stimulation, the ALP of MC3T3-E1 increased significantly under the treatment of recombinant human secretory DDRGK1 (containing SEQ ID NO: 2 and SEQ ID NO: 1);

On the 7$^{th}$ day of stimulation, the Col-1 of MC3T3-E1 increased significantly under the treatment of recombinant human secretory DDRGK1 (containing SEQ ID NO: 2 and SEQ ID NO: 1);

On the 7$^{th}$ day of stimulation, the OCN of MC3T3-E1 increased significantly under the treatment of recombinant human secretory DDRGK1 (containing SEQ ID NO: 2 and SEQ ID NO: 1);

On the 7$^{th}$ day of stimulation, the RUNX2 of MC3T3-E1 increased significantly under the treatment of recombinant human secretory DDRGK1 (containing SEQ ID NO: 2 and SEQ ID NO: 1);

The results show that recombinant human secretory DDRGK1 (containing SEQ ID NO: 2 and SEQ ID NO: 1) is capable of improving the expression of the osteogenic differentiation marker mRNA of mouse MC3T3-E1 cell line.

Figure 15:
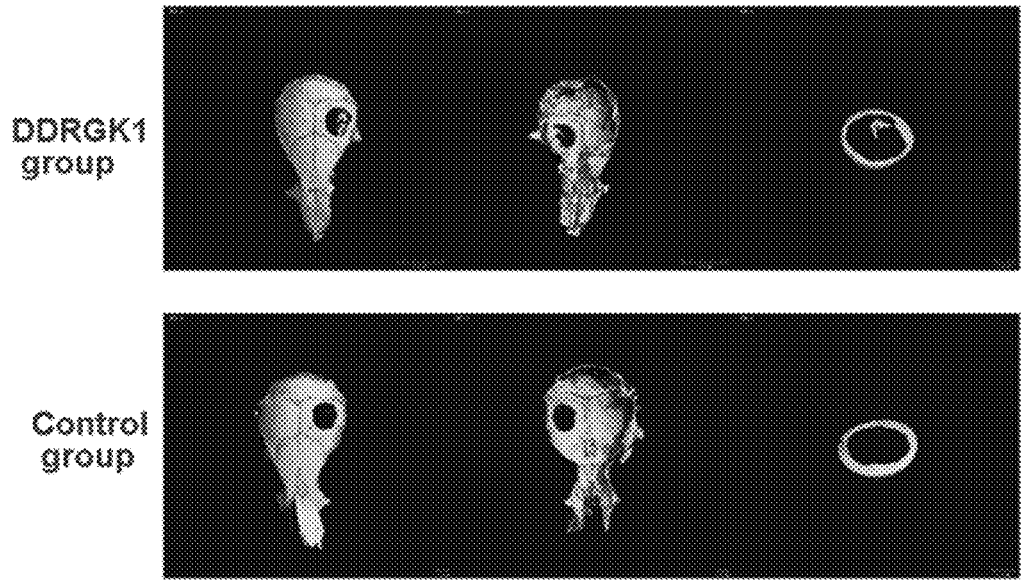
FIG. 15 shows the repair of mouse skull defect model by recombinant human secretory DDRGK1 (containing SEQ ID NO: 2 and SEQ ID NO: 1).

3.13 Repair Effect of Recombinant Human Secretory DDRGK1 (Containing SEQ ID NO: 2 and SEQ ID NO: 1) on Mouse Skull Defect Model Micro-CT shows (FIG. 15) that under the treatment of recombinant human secretory DDRGK1 (containing SEQ ID NO: 2 and SEQ ID NO: 1), the skull was significantly repaired compared with the control group. The result indicates that the recombinant human secretory DDRGK1 (containing SEQ ID NO: 2 and SEQ ID NO: 1) can promote the repair of mouse skull defects.

What is claimed is:

1. A recombinant human secretory DDRGK1 comprising: SEQ ID NO: 1 linked at its N-terminus to SEQ ID NO: 2.

2. The recombinant human secretory DDRGK1 of claim 1, wherein a C-terminus of SEQ ID NO: 1 is linked to SEQ ID NO: 3, and wherein SEQ ID NO: 3 is further linked to SEQ ID NO: 4.

3. A pharmaceutical composition comprising a therapeutically effective amount of the recombinant human secretory DDRGK1 of claim 1, and a pharmaceutically acceptable carrier.

4. The pharmaceutical composition of claim 3, wherein the pharmaceutical composition is in the form of an injection, a subcutaneous implant, a tablet, powder, a granule, a capsule, an oral liquid, or a slow-released formulation.

5. A method for the treatment of intervertebral disc degeneration, chondrogenic degeneration, or fractures and bone defects comprising:

administering an effective amount of the recombinant human secretory DDRGK1 of claim 1 to a subject in need thereof.

* * * * *

SEQUENCE LISTING

```
<160> NUMBER OF SEQ ID NOS: 4

<210> SEQ ID NO 1
<211> LENGTH: 286
<212> TYPE: PRT
<213> ORGANISM: Artificial Sequence
<220> FEATURE:
<223> OTHER INFORMATION: coressponding to truncated human DDRGK1 cDNA
      fragment encoding amino acid residues in which positions 1-28 are
      deleted

<400> SEQUENCE: 1

Ala Ser Ala Gly Gln Glu Pro Leu His Asn Glu Glu Leu Ala Gly Ala
1               5                   10                  15

Gly Arg Val Ala Gln Pro Gly Pro Leu Glu Pro Glu Glu Pro Arg Ala
            20                  25                  30

Gly Gly Arg Pro Arg Arg Arg Asp Leu Gly Ser Arg Leu Gln Ala
        35                  40                  45

Gln Arg Arg Ala Gln Arg Val Ala Trp Ala Glu Ala Asp Glu Asn Glu
    50                  55                  60

Glu Glu Ala Val Ile Leu Ala Gln Glu Glu Gly Val Glu Lys Pro
65                  70                  75                  80

Ala Glu Thr His Leu Ser Gly Lys Ile Gly Ala Lys Lys Leu Arg Lys
                85                  90                  95

Leu Glu Glu Lys Gln Ala Arg Lys Ala Gln Arg Glu Ala Glu Glu Ala
            100                 105                 110

Glu Arg Glu Glu Arg Lys Arg Leu Glu Ser Gln Arg Glu Ala Glu Trp
        115                 120                 125

Lys Lys Glu Glu Glu Arg Leu Arg Leu Glu Glu Glu Gln Lys Glu Glu
    130                 135                 140

Glu Glu Arg Lys Ala Arg Glu Glu Gln Ala Gln Arg Glu His Glu Glu
145                 150                 155                 160

Tyr Leu Lys Leu Lys Glu Ala Phe Val Val Glu Glu Glu Gly Val Gly
                165                 170                 175

Glu Thr Met Thr Glu Glu Gln Ser Gln Ser Phe Leu Thr Glu Phe Ile
            180                 185                 190

Asn Tyr Ile Lys Gln Ser Lys Val Val Leu Leu Glu Asp Leu Ala Ser
        195                 200                 205

Gln Val Gly Leu Arg Thr Gln Asp Thr Ile Asn Arg Ile Gln Asp Leu
```

```
                210                 215                 220
Leu Ala Glu Gly Thr Ile Thr Gly Val Ile Asp Asp Arg Gly Lys Phe
225                 230                 235                 240

Ile Tyr Ile Thr Pro Glu Glu Leu Ala Ala Val Ala Asn Phe Ile Arg
                245                 250                 255

Gln Arg Gly Arg Val Ser Ile Ala Glu Leu Ala Gln Ala Ser Asn Ser
                260                 265                 270

Leu Ile Ala Trp Gly Arg Glu Ser Pro Ala Gln Ala Pro Ala
                275                 280                 285

<210> SEQ ID NO 2
<211> LENGTH: 16
<212> TYPE: PRT
<213> ORGANISM: Artificial Sequence
<220> FEATURE:
<223> OTHER INFORMATION: membrane-spanning signal peptide

<400> SEQUENCE: 2

Met Lys Thr Ile Ile Ala Leu Ser Tyr Ile Phe Cys Leu Val Phe Ala
1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: TEV restriction enzyme cutting site

<400> SEQUENCE: 3

Glu Asn Leu Tyr Phe Gln Gly
1               5

<210> SEQ ID NO 4
<211> LENGTH: 8
<212> TYPE: PRT
<213> ORGANISM: Artificial Sequence
<220> FEATURE:
<223> OTHER INFORMATION: purification tag

<400> SEQUENCE: 4

His His His His His His His His
1               5
```